US012708346B2

(12) United States Patent
Savord et al.

(10) Patent No.: US 12,708,346 B2
(45) Date of Patent: Aug. 18, 2026

(54) ULTRASOUND IMAGING SYSTEM HAVING DIGITAL ULTRASONIC IMAGING DEVICES

(71) Applicant: KONINKLIJKE PHILIPS N.V., Eindhoven (NL)

(72) Inventors: Bernard Joseph Savord, Andover, MA (US); Thomas James Hunt, Pelham, NH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 18/863,025

(22) PCT Filed: May 1, 2023

(86) PCT No.: PCT/EP2023/061424
§ 371 (c)(1),
(2) Date: Nov. 5, 2024

(87) PCT Pub. No.: WO2023/213748
PCT Pub. Date: Nov. 9, 2023

(65) Prior Publication Data
US 2025/0312009 A1 Oct. 9, 2025

Related U.S. Application Data

(60) Provisional application No. 63/338,519, filed on May 5, 2022.

(51) Int. Cl.
*A61B 8/00* (2006.01)
*A61B 8/06* (2006.01)

(52) U.S. Cl.
CPC .............. *A61B 8/4494* (2013.01); *A61B 8/06* (2013.01); *A61B 8/488* (2013.01); *A61B 8/565* (2013.01)

(58) Field of Classification Search
CPC ......... A61B 8/4494; A61B 8/06; A61B 8/488; A61B 8/565; A61B 8/483; A61B 8/56;
(Continued)

(56) References Cited

U.S. PATENT DOCUMENTS 6,500,126 B1 * 12/2002 Brock-Fisher ........... A61B 8/00 600/459
2004/0179332 A1 * 9/2004 Smith .................... A61B 50/13 361/679.41

(Continued)

FOREIGN PATENT DOCUMENTS

WO 2004080364 A2 9/2004
WO 2021259714 A1 12/2021
WO 2022069264 A1 4/2022

OTHER PUBLICATIONS

International Search Report and Written Opinion for PCT/EP2023/061424, Mailing date: Jul. 27, 2023, 13 pages.

(Continued)

*Primary Examiner* — Alexei Bykhovski

(57) ABSTRACT

An ultrasound (US) imaging system (100) is disclosed. The US imaging system (100) includes an ultrasound imaging device (110) comprising a transducer; and a digital transducer interface (DTI (206)). The DTI (206) includes a plurality of transducer ports (309) each comprising a plurality of digital data streams adapted to transmit digitized echo output data from the ultrasound imaging device (110). The transducer ports (309) are adapted to connect to the ultrasound imaging device (110). The US system also includes: a switching circuit (301) connected to each of the plurality of transducer ports (309); and a controller (102) adapted to control switches (24) of the switching circuit (301) to transmit digital input data to and the digital echo output data from one of the plurality of transducer ports (309) at a time.

17 Claims, 8 Drawing Sheets

(58) Field of Classification Search
CPC ............... G01S 7/52017; G01S 7/5203; G01S 7/52079; G01S 7/52082
See application file for complete search history.

(56) References Cited

U.S. PATENT DOCUMENTS

| | | | | |
|---|---|---|---|---|
| 2005/0203404 | A1* | 9/2005 | Freiburger | G01S 7/5208 600/453 |
| 2014/0114190 | A1* | 4/2014 | Chiang | A61B 8/468 600/440 |
| 2019/0196011 | A1 | 6/2019 | Brodsky et al. | |
| 2020/0100766 | A1 | 4/2020 | Solek | |
| 2020/0138414 | A1 | 5/2020 | Maurice et al. | |
| 2020/0352546 | A1 | 11/2020 | Dickie et al. | |
| 2021/0093299 | A1 | 4/2021 | Heid | |
| 2021/0386404 | A1* | 12/2021 | Walker | G01S 7/52046 |
| 2022/0225966 | A1* | 7/2022 | Raju | G16H 30/40 |
| 2023/0273306 | A1 | 8/2023 | Savord | |

OTHER PUBLICATIONS

Hager, P. A. et al., "LightProbe: A Digital Ultrasound Probe for Software-Defined Ultrafast Imaging," IEEE Transactions on Ultrasonics, Ferroelectrics, and Frequency Control, 2019, vol. 66, No. 4, pp. 747-760.

Kidav, J. et al., "Design of a 128-channel transceiver hardware for medical ultrasound imaging systems," IET Circuits Devices & Systems, 2022, vol. 16, pp. 92-104.

* cited by examiner

ULTRASOUND IMAGING SYSTEM HAVING DIGITAL ULTRASONIC IMAGING DEVICES

CROSS-REFERENCE TO PRIOR APPLICATIONS

This application is the U.S. National Phase application under 35 U.S.C. § 371 of International Application No. PCT/EP2023/061424, filed on May 1, 2023, which claims the benefit of U.S. Provisional Patent Application No. 63/338,519, filed on May 5, 2022. These applications are hereby incorporated by reference herein.

BACKGROUND

Ultrasound (US) imaging is ubiquitous in a variety of applications, including medical imaging. US imaging devices often comprise an array of piezoelectric transducers for making a variety of different measurements. Cart based imaging systems typically have four identical transducer connectors for user convenience whereby multiple transducers for imaging different anatomies can remain connected and the user picks up the desired transducer and activates it by pressing a button on the user interface.

Transducer connectors in current cart-based systems connect analog signals from analog transducers. These connectors typically have a large number of connections and a performance limited by the number of analog processing channels within the system. Digital ultrasound transducers whereby digitization of ultrasound data is performed within the transducer, have the potential to reduce the number of connections by multiplexing ultrasound data from multiple transducer elements into fewer high speed digital connections. Since there is no longer analog processing channels within the system, image quality is not constrained by the system.

Digital USB based ultrasound devices available today have limited performance due to the single data stream with insufficient data rates for premium imaging performance. These devices also typically use a single connector port.

Transducers that support different anatomies have different data rate requirements and use different integrated circuit technology requiring different voltages to power them. To keep the transducer connecting cable small and light weight, low diameter conductors are used that have a significant loss in the power supply wires. Some of these transducers support continuous wave (CW) Doppler measurements that use analog based band quadrature outputs.

What is needed is a system that overcomes at least the noted drawbacks of known systems set forth above.

SUMMARY

According to an aspect of the present disclosure, an ultrasound (US) imaging system is disclosed. The US imaging system comprises: an ultrasound imaging device comprising a transducer; and a digital transducer interface (DTI). The DTI comprises: a plurality of transducer ports each comprising a plurality of digital data streams adapted to transmit digitized echo output data from the ultrasound imaging device. The transducer ports are adapted to connect to the ultrasound imaging device. The US system also comprises: a switching circuit connected to each of the plurality of transducer ports; and a controller adapted to control switches of the switching circuit to transmit digital input data to and the digital echo output data from one of the plurality of transducer ports at a time.

According to another aspect of the present disclosure, a DTI is disclosed. The DTI comprises: a plurality of transducer ports each comprising a plurality of digital data streams adapted to transmit digitized echo output data from the ultrasound imaging device. The transducer ports are adapted to connect to the ultrasound imaging device. The US system also comprises: a switching circuit connected to each of the plurality of transducer ports; and a controller adapted to control switches of the switching circuit to transmit digital input data to and the digital echo output data from one of the plurality of transducer ports at a time.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

As used in the specification and appended claims, and in addition to their ordinary meanings, the term 'approximately' mean to with acceptable limits or degree. For example, "approximately 20 GHz" means one of ordinary skill in the art would consider the signal to be 20 GHz within reasonable measure.

As used in the specification and appended claims, in addition to their ordinary meanings, the term 'substantially' means within acceptable limits or degree. For example, the "plurality of transducer ports are substantially the same" means one of ordinary skill in the art would consider the plurality of transducer ports to be the same.

Figure 1:
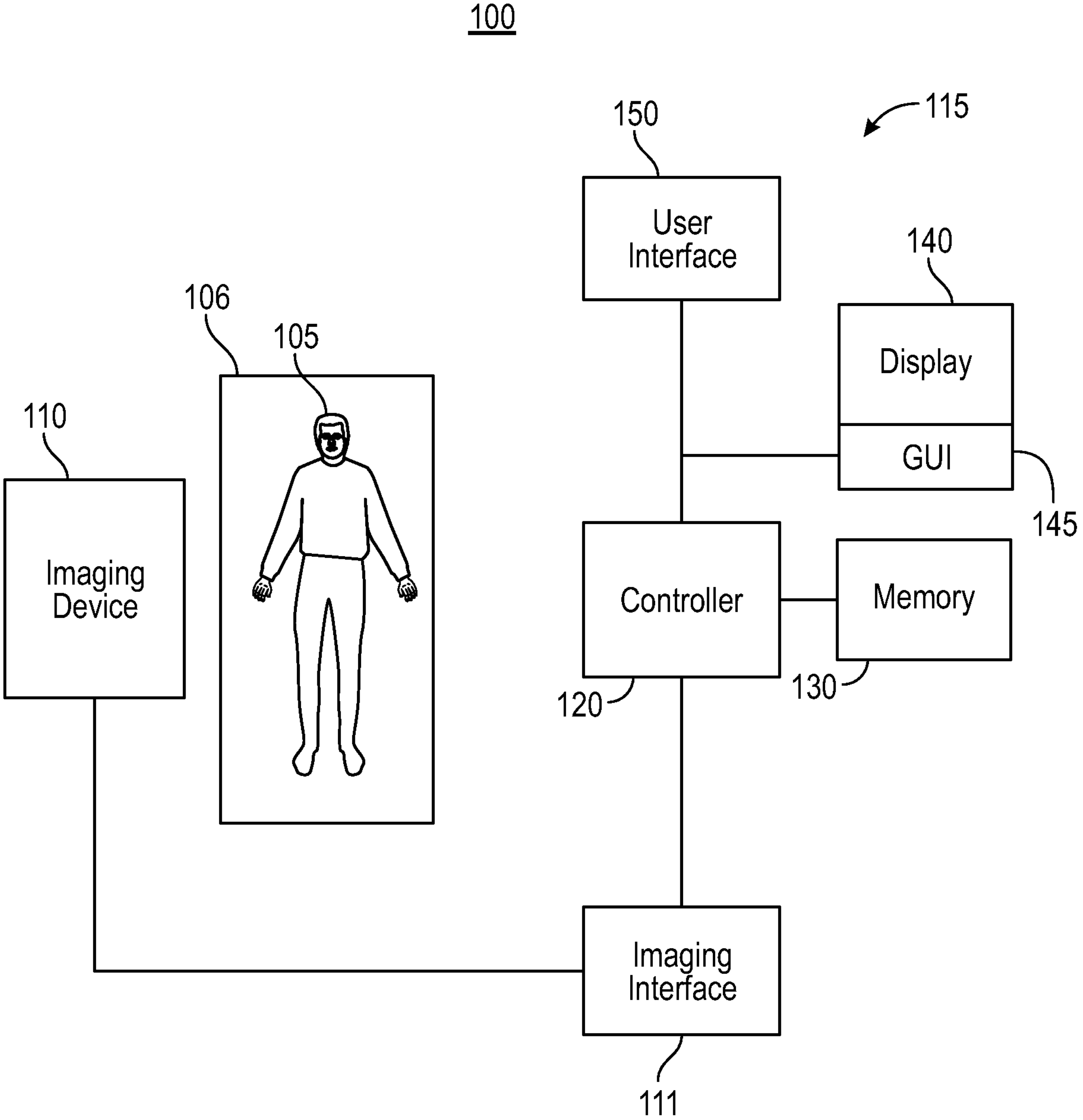
FIG. 1 is a simplified block diagram of an US imaging system for imaging a portion of a body, according to a representative embodiment.

FIG. 1 is a simplified block diagram of an imaging system 100 for imaging a region of interest of a subject, according to a representative embodiment.

Referring to FIG. 1, the imaging system 100 comprises an imaging device 110 and a computer system 115 for controlling imaging of a region of interest in a patient 105 on a table 106. The imaging device 110 is illustratively an ultrasound imaging system capable of providing an ultrasound (US) image scan of a region of interest in the patient 105. Illustratively, the imaging device 110 is of the type commonly used in US imaging procedures. The imaging device 110 is adapted to provide color Doppler imaging or three dimensional flow volumetry imaging or continuous wave (CW) Doppler measurements. As described more fully below, the imaging device 110 illustratively comprises a transducer array that may include capacitive micromachined ultrasonic transducers (CMUTs) or piezoelectric transducers formed of materials such as PZT or PVDF, for example. The transducer array may be coupled to a microbeamformer (not shown) in the imaging device, and controls reception of signals by the transducers.

In certain embodiments, the imaging device 110 may be as described in commonly owned International Patent Application Publication No. WO2022069264 and U.S. Provisional Application No. 63/084,728 filed on Sep. 29, 2020. The entire disclosures of International Patent Application Publication No. WO2022069264 and U.S. Provisional Application No. 63/084,728 are specifically incorporated herein by reference (copies of these documents are attached to this filing).

The computer system 115 receives image data from the imaging device 110, and stores and processes the imaging data according to representative embodiments described herein. The computer system 115 comprises a controller 120, a memory 130, a display 140 comprising a graphical user interface (GUI) 145, and a user interface 150. The display 140 may also include a loudspeaker (not shown) to provide audible feedback.

The controller 120 interfaces with the imaging device 110 through an imaging interface 111. The imaging interface 111 comprises a digital transducer interface (DTI) (not shown in FIG. 1) and enables the connection and operation at comparatively high data rate transmission of digital data to and from a variety of imaging devices 110 contemplated for use in the US imaging system 100. As described more fully below in connection with various representative embodiments, the DTI comprises a plurality of ports and enables operation of a selected one of multiple imaging devices 110 operating at comparatively high data rates in the US imaging system 100. The DTI of the imaging interface 111 enables switching at high data speed between the multiple imaging devices 110, as well as receiving high data rate echo imaging data for further digital signal processing. In one aspect, the imaging interface 111 enables the implementation of a variety of imaging devices 110 employing multiple digital technologies requiring different voltages. Moreover, in accordance with a representative embodiment, the DTI of the imaging interface 111 enables compensation for voltage drops in cables connecting the imaging device 110 between the computer system 115 and the imaging device 110. Furthermore, and again as described more fully below, the DTI of the imaging interface 111 enables operation of an imaging device 110 adapted to perform CW Doppler imaging, in addition to the described digital US imaging devices 110 of the present teachings.

The memory 130 stores instructions executable by the controller 120. When executed, and as described more fully below, the instructions cause the controller 120 to allow the user to perform different steps using the GUI 145 or the user interface 150, or both, and, among other tasks, to initialize an ultrasound imaging device comprising a transducer. In addition, the controller 120 may implement additional operations based on executing instructions, such as instructing or otherwise communicating with another element of the computer system 115, including the memory 130 and the display 140, to perform one or more of the above-noted processes.

The controller 120 is representative of one or more processing devices, and is configured to execute software instructions stored in memory 130 to perform functions as described in the various embodiments herein. The controller 120 may be implemented by field programmable gate arrays (FPGAs), application specific integrated circuits (ASICs), systems on a chip (SOC), a general purpose computer, a central processing unit, a computer processor, a microprocessor, a graphics processing unit (GPU), a microcontroller, a state machine, programmable logic device, or combinations thereof, using any combination of hardware, software, firmware, hard-wired logic circuits, or combinations thereof. Additionally, any processing unit or processor herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems, such as in a cloud-based or other multi-site application. The term computing device should also be interpreted to include a collection or network of computing devices each including a processor or processors. Programs have software instructions performed by one or multiple processors that may be within the same computing device or which may be distributed across multiple computing devices.

The memory 130 may include a main memory and/or a static memory, where such memories may communicate with each other and the controller 120 via one or more buses. The memory 130 stores instructions used to implement some or all aspects of methods and processes described herein. The memory 130 may be implemented by any number, type and combination of random access memory (RAM) and read-only memory (ROM), for example, and may store various types of information, such as software algorithms, which serves as instructions, which when executed by a processor cause the processor to perform various steps and methods according to the present teachings. Furthermore, updates to the methods and processes described herein may also be provided to the computer system 115 and stored in memory 130.

The various types of ROM and RAM may include any number, type and combination of computer readable storage media, such as a disk drive, flash memory, an electrically programmable read-only memory (EPROM), an electrically erasable and programmable read only memory (EEPROM), registers, a hard disk, a removable disk, tape, compact disk read only memory (CD-ROM), digital versatile disk (DVD), floppy disk, Blu-ray disk, a universal serial bus (USB) drive, or any other form of storage medium known in the art. The memory 130 is a tangible storage medium for storing data and executable software instructions, and is non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The memory 130 may store software instructions and/or computer readable code that enable performance of various functions. The memory 130 may be secure and/or encrypted, or unsecure and/or unencrypted.

"Memory" is an example of computer-readable storage media, and should be interpreted as possibly being multiple memories or databases. The memory or database for instance may be multiple memories or databases local to the computer, and/or distributed amongst multiple computer systems or computing devices. A computer readable storage medium is defined to be any medium that constitutes patentable subject matter under 35 U.S.C. § 101 and excludes any medium that does not constitute patentable subject matter under 35 U.S.C. § 101. Examples of such media include non-transitory media such as computer memory devices that store information in a format that is readable by a computer or data processing system. More specific examples of non-transitory media include computer disks and non-volatile memories.

The user interface 150 may include a user and/or network interface for providing information and data output by the controller 120 and/or the memory 130 to the user and/or for receiving information and data input by the user. That is, the user interface 150 enables the user to operate the imaging device as described herein, and to schedule, control or manipulate aspects of the imaging system 100 of the present teachings. Notably, the user interface 150 enables the controller 120 to indicate the effects of the user's control or manipulation. The user interface 150 may include one or more of ports, disk drives, wireless antennas, or other types of receiver circuitry. The user interface 150 may further connect one or more interface devices, such as a mouse, a keyboard, a mouse, a trackball, a joystick, a microphone, a video camera, a touchpad, a touchscreen, voice or gesture recognition captured by a microphone or video camera, for example.

The display 140 may be a monitor such as a computer monitor, a television, a liquid crystal display (LCD), a light emitting diode (LED) display, a flat panel display, a solid-state display, or a cathode ray tube (CRT) display, or an electronic whiteboard, for example. The display 140 may also provide a graphical user interface (GUI) 145 for displaying and receiving information to and from the user.

Figure 2:
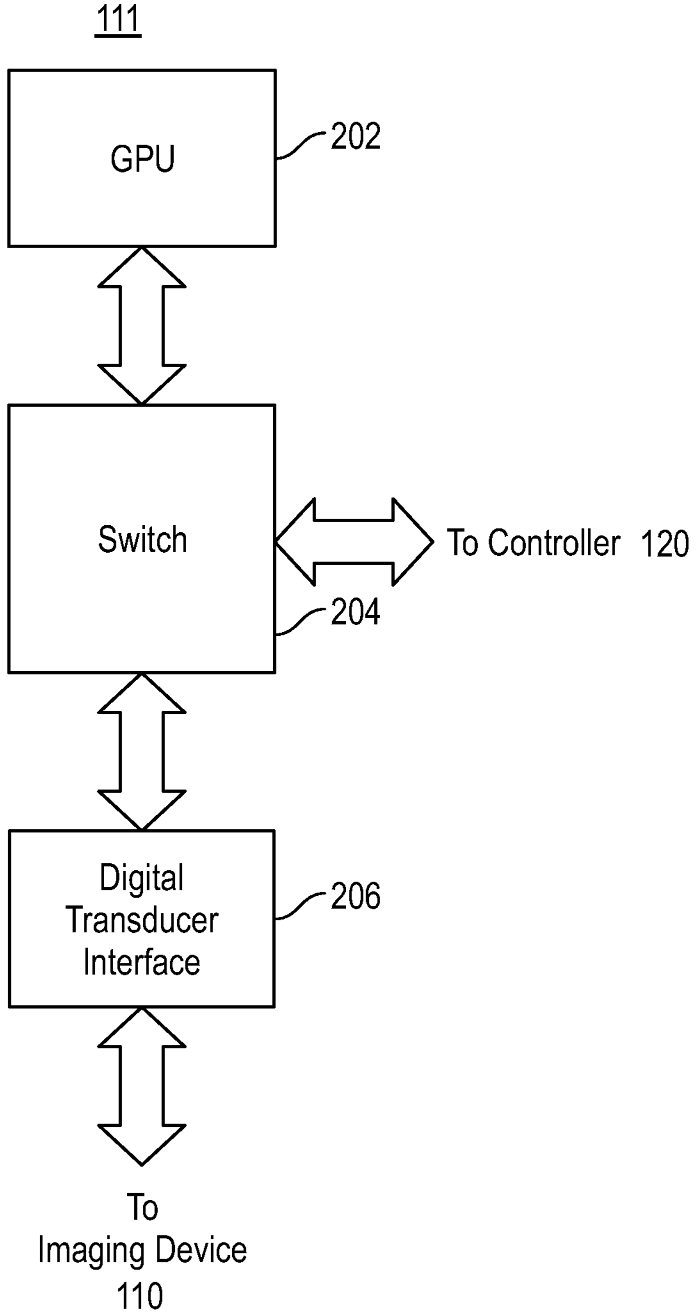
FIG. 2 is a simplified block diagram of an imaging interface for use in an US imaging system according to a representative embodiment.

FIG. 2 is a simplified block diagram of imaging interface 111 for use in an US imaging system according to a representative embodiment. Various aspects and details of the imaging interface are common to those described in connections with the US imaging system 100 described above. These common aspects and details may not be repeated to avoid obscuring the presently described representative embodiment.

The imaging interface 111 beneficially comprises a graphics processor unit (GPU) 202, a switch 204 and a digital transducer interface (DTI) 206. The DTI 206 comprises a comparatively high data rate interface to the switch 204. As described more fully below, the DTI 206 converts the input data from the US imaging device 110 to a digital format, in which each signal corresponds to each transducer element of the transducer phased arrays of the imaging device 110.

Data transfer between the imaging device 110, the DTI 206, the switch 204, the GPU 202 and the controller 120 is carried out using a comparatively high bandwidth interface in view of the bandwidth requirements of the digital echo output signals of current imaging devices 110. To this end, transmission of digital echo output data requires significant bandwidth, and cannot be properly effected over many known comparatively low bandwidth data transmission platforms. As described more fully below, the DTI 206 receives data from the imaging device 110 at a rate of at least approximately 20 Gigabits/sec (Gbps). In some representative embodiments, the data rate at which the DTI 206 receives data from the imaging device 110 is in the range of at least approximately 20 Gbps to approximately 150 Gbps. In certain other embodiments, the data rate at which the DTI 206 receives data from the imaging device 110 is approximately 256 Gbps. Moreover, the DTI 206 is adapted to provide input data to the imaging device 110 at a data rate of approximately 1 Gbps to approximately 32 Gbps because less data are needed to program the imaging device 110.

In accordance with a representative embodiment, data transfer between the imaging device 110, the DTI 206, the switch 204, the GPU 202 and the controller 120 is effected using a high-speed data interconnect, such as Peripheral Component Interconnect Express (PCIe) interconnect, or bus with the link between devices having one to 16 lanes for transmission of serial data from the imaging device 110 and the computer system 115 of the US system. Notably, to accommodate the desired comparatively high data rate transmission, serial links are beneficial to avoid timing skew. Notably, other known high-speed serial computer expansion bus standards may be used. Specifically, in order to accommodate the high data rate transfer in the imaging system 100, bandwidth limitations in the serial signals are greater than approximately 20 Gbps.

PCIe devices communicate via a logical connection called an interconnect or link. A link is a point-to-point communication channel between two PCIe ports allowing both of them to send and receive ordinary PCI requests (configuration, I/O or memory read/write) and interrupts (INTx, MSI or MSI-X). At the physical level, a link is composed of one or more lanes. A lane comprises two differential signaling pairs, with one pair for receiving data and the other for transmitting. Thus, each lane is composed of four wires or signal traces. Conceptually, each lane is used as a full-duplex byte stream, transporting data packets in eight-bit "byte" format simultaneously in both directions between endpoints of a link. Physical PCI Express links may contain 1, 4, 8 or 16 lanes. As is known, lane counts are written with an "x" prefix (for example, "x8" represents an eight-lane card or slot), with ×16 being the largest size in common use. Lane sizes are also referred to via the terms "width" or "by" e.g., an eight-lane slot could be referred to as a "by 8" or as "8 lanes wide." While the number of lanes being used is not limited by the present teachings, in accordance with a representative embodiment in which graphical data are transmitted from the imaging device 110 and ultimately to the computer system 115, a comparative wide lane system is beneficial for more rapid data transmission. Just by way of illustration, connections from the US device to the GPU 202 are carried out using a 16-lane (×16) link.

PCIe is just one example of the general trend toward replacing parallel buses with serial interconnects; other examples include but are not limited to Serial ATA (SATA), Serial Attached SCSI (SAS), FireWire (IEEE 1394), and RapidIO. In digital video, examples in common use are DVI, HDMI and DisplayPort. Furthermore, multichannel serial design increases flexibility with its ability to allocate fewer lanes for slower devices.

In accordance with a representative embodiment, data received from the DTI 206 are provided over the PCIe interconnect to the switch 204. The switch 204 is a PCIe switch that is adapted to transmit the data to the GPU 202 and to the controller 120, as well as from the GPU 202 and the controller 120 to the DTI 206 at the data rates characteristic of PCIe interconnects.

The GPU 202 performs known beamforming steps by ordered processing of the digital echo output signals from the imaging device 110 for display by the US imaging system 100. The GPU 202 may then effect scan conversion of the digital echo output signals from the imaging device 110 to a desired format for display by the US imaging system 100. The output from the GPU 202 is then provided by the switch 204 and then to the controller 120 of the US imaging system 100. Alternatively, the digital echo output data from the imaging device 110 may be transferred by the switch 204 to the controller 120.

Figure 3:
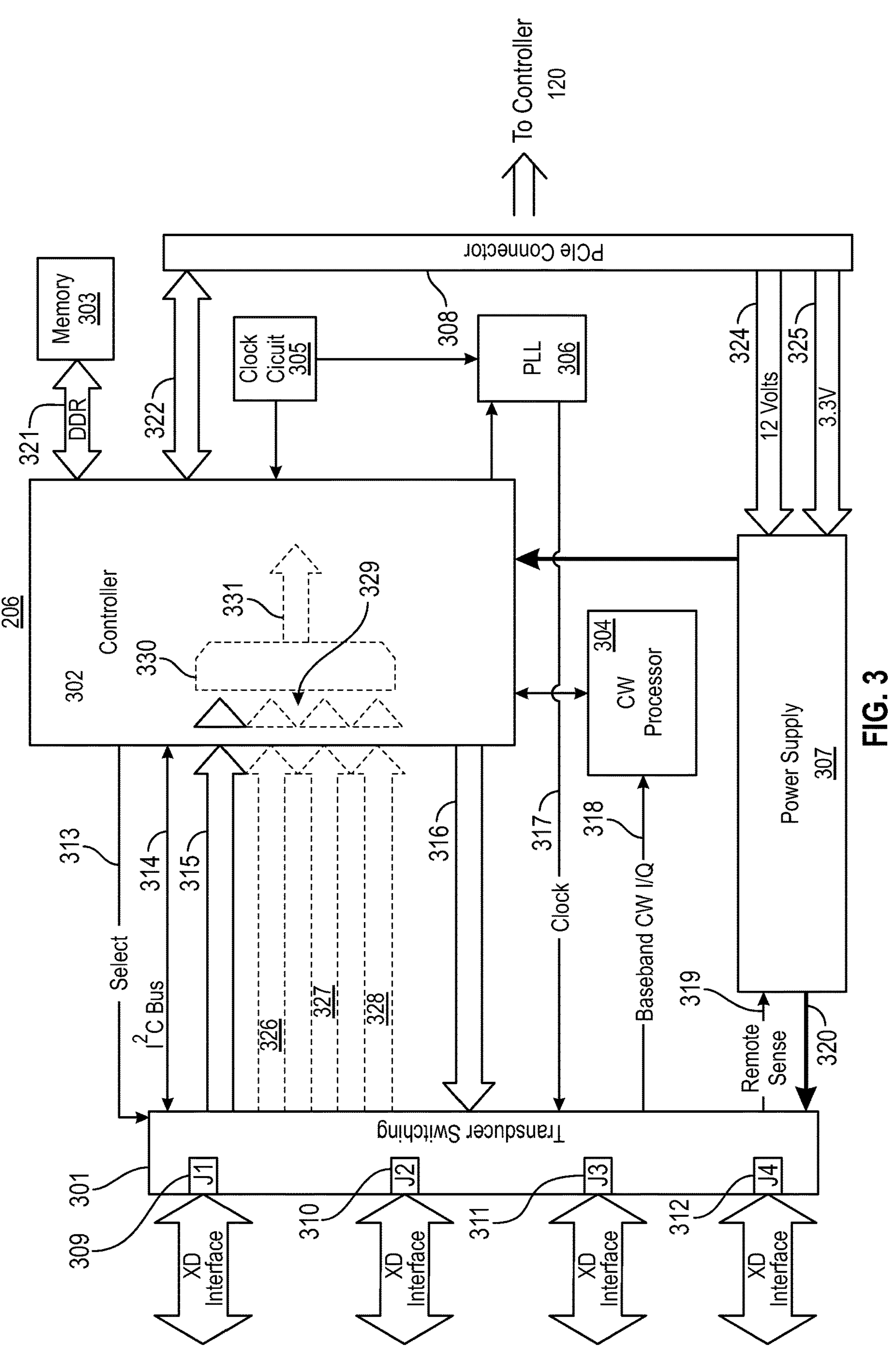
FIG. 3 is a simplified block diagram of a digital transducer interface (DTI) for use in an US imaging system according to a representative embodiment.

FIG. 3 is a simplified block diagram of DTI 206 for use in an US imaging system according to a representative embodiment. Various aspects and details of the imaging interface are common to those described in connection with the US imaging system 100 and imaging interface 111 the described above. These common aspects and details may not be repeated to avoid obscuring the presently described representative embodiments.

The DTI 206 comprises a switching circuit 301. As described more fully below, the switching circuit 301 comprises a plurality of switches (not shown in FIG. 3) to enable connection of transducers of an imaging device 110 with the DTI 206.

The DTI 206 also comprises a controller 302 and a memory 303. In a representative embodiment, the controller 302 comprises an FPGA that functions as a processor (e.g., a multi-core processor) or comprises a processor, and the memory 303 comprises a computer readable medium that stores instructions. In addition to storing executable instructions (code), the memory 303 is also adapted to function as a buffer data received from the transducers of the imaging device 110. Notably, the rate of reception of output digital echo image data from the imaging device 110 may be greater than the capabilities of the controller 120, so buffering of image digital echo data in the memory can be beneficial.

The DTI 206 further comprises a clock circuit 305 and a phase lock loop (PLL) 306 to provide an external timing function to the controller 302. Beneficially, the PLL 306 enables the generation of a comparatively low jitter/low noise timing signal to be provided to the controller 102 and enables comparatively precise transmission and reception of data to and from the controller 302. Beneficially, the frequency of this PLL 306 is programmable to allow for interfacing to transducers with different data rate requirements. The timing signal from the clock circuit 305, among other functions, is used in the configuration of the selected imaging device 110 upon selection by the user. As such, control and data signals provided by the controller 302 are transmitted based on timing set by the clock circuit 305.

The DTI 206 further comprises a power supply 307. The power supply 307 provides the requisite power to the imaging device 110. Notably, and as described more fully below, the power supply 307 is adapted to compensate for a voltage drop caused by the electrical connection (e.g., cable) between the power supply 307 and the imaging device 110.

As described more fully below, the controller 302 executes instructions to effect connections between the DTI 206 and the imaging device 110. These connections enable the transmission of input data to the imaging device 110, and the reception of output digital echo data from the imaging device 110. Notably, when an FPGA is used for the controller 302, the FPGA would be programmed to carry out the various functions described herein. The use of an FPGA for the controller 302 is merely illustrative. More generally, the controller 302 may comprise a system-on-a-chip (SOC) comprising a processor that executes the instructions stored in memory 303 to enable the configuration of the switches of the switching circuit 301 to effect configuration of the selected type of imaging device 110 and transmission and reception of data to/from the imaging device 110 by the DTI 206. Controller 302 may also be a custom design integrated circuit.

The DTI 206 further comprises a continuous wave (CW) processor 304, which, as described more fully below, is adapted to receive in-phase (I) and quadrature (Q) analog imaging data from the imaging device 110.

The DTI 206 further comprises a connector 308 to provide data/signal transfer between the computer system 115 and the imaging device 110 of the imaging system 100. In keeping with a representative embodiment described above, the connector 308 comprises components adapted for transmission of data along a PCIe bus.

The DTI 206 further comprises a plurality of transducer ports 309~312 each comprising a plurality of digital data streams adapted to transmit digitized echo output data from the ultrasound imaging device, and to transmit control and data signals from the controller 302. In the illustrative embodiment of FIG. 3, four transducer ports are depicted. It is emphasized that this is merely illustrative, and more or fewer ports may be used depending on the requirements of the imaging system 100. The plurality of transducer ports 309~312 labeled J1~J4 are substantially identical and are adapted to transmit comparatively high speed serial digital between the transducers of the imaging device 110 and the computer system 115 of the US imaging system 100. As discussed more fully below, each of the plurality of transducer ports 309~312 is selected to be compatible with the selected transmission platform. By way of illustration, the physical layer may use 24 current mode logic (CML) differential pairs. As such, in accordance with a representative embodiment, the selected transmission platform comprises 24 streams of CML differential pairs. Notably, CML happens to be the same physical layer as used in PCIe. However, PCIe also includes a complex Protocal layer, which is not included in this interface.

The plurality of transducer ports 309~312 are also adapted to receive control data and clock signals from the clock circuit 305. Moreover, each of the plurality of transducer ports 309~312 are adapted to receive baseband CW data, as noted below.

As alluded to above, in accordance with a representative embodiment a selected one of the plurality of transducer ports 309~312 is engaged at a time. To this end, a user selects a particular imaging device 110 to perform an exam on a patient. Upon selection of the imaging device 110, the user connects the imaging device 110 to a selected port (e.g., J1). As described more fully below, upon selection of the particular transducer port for connection of the imaging device 110, the controller 302 activates switches (not shown in FIG. 3) to engage the selected one of the plurality of transducer ports 309~312 to engage the selected the imaging device 110 with the imaging system 100 and enable the US exam to be carried out. Notably, an $I^2C$ bus 314 may be used to communicate low bandwidth information such as transducer identification, serial number, operating temperature and status.

Connections between the selected one of the plurality of transducer ports 309~312 are made using interconnect 315, which transmits output digital echo image data from the imaging device 110, and interconnect 316, which transmits control and signals from the computer system 115 and the selected imaging device. Interconnects 315, 316 are selected to be compatible with the selected transmission platform of the DTI 206. For example, in view of the comparatively high demands of bandwidth for reception of output digital echo image data from the imaging device 110, the interconnect 315 is illustratively 24 differential pairs of CML or similar comparatively high data rate interconnect. Similarly, in order to transmit control and data signals from the controller 302 to the imaging device 110, the interconnect 316 is illustratively of 8 low voltage differential signal (LVDS) pairs or similar comparatively high data rate interconnect. Moreover, interconnects 315, 316 each provide a plurality of data streams through the selected one of the plurality of transducer ports 309~312 to enable data transmission/reception at a combined data rate greater than approximately 20 Gbps as contemplated by the present teachings. Again, by way of illustration, when implemented using CML differential pairs, interconnects 315, 316 may have as many as 32 lanes to provide the plurality of data streams at the needed data transmission rates to carry out the desired imaging by the US imaging system 100.

In accordance with a representative embodiment, after selection by the user, the imaging device 110 is configured based on control and data signals from the user via the computer system 115. As alluded to above, the DTI 206 enables comparatively high data rate exchange of data and signals between the selected imaging device 110 and the user of the imaging system 100. As such, the interconnect 315 is a serial interface and does not exhibit timing skew because there is only one differential signal in each direction within each lane, and there is no external clock signal since clocking information is embedded within the serial signal itself. Notably, the clock is used to clock logic within the imaging device 110.

Baseband CW data from the imaging device 110 is transmitted via baseband CW interface 318. By selection of the appropriate switches in the switching circuit 301, the baseband CW I/Q data can be provided through the selected one of the plurality of transducer ports 309~312 to the DTI 206 and ultimately to the user at the computer system 115 of the imaging system 100. Baseband CW is often used to measure blood flow in a body by continuous transmission of ultrasound energy into the body and make measurements based on Doppler shifts with reflected sound waves. As will be appreciated by one of ordinary skill in the art, baseband CW ultrasound often requires a comparatively high dynamic range. As such, the baseband CW interface 318 is illustratively an analog link, which accords the required comparatively high dynamic range of CW signals from the imaging device 110.

Also connected through the selected one of the plurality of transducer ports 309~312 is the power supply 307. Notably, based on input signals 324, 325, the power supply 307 provides the requisite power to the selected imaging device 110 through interface 320. The raw input voltage to these power supplies comes from the 12V and 3.3V defined in the PCIe standard and are provided over the connector 308

Moreover, the power supply 307 also receives a remote sense signal 319 from the selected one of the plurality of transducer ports 309~312 connected by the selected switches of the switching circuit 301. The remote sense signal 319 provides the measured voltage level at the transducer head of the imaging device 110. This measured voltage is provided by the power supply 307 to the controller 302. Based on the length of the cable connecting the imaging device 110 to the selected one of the plurality of transducer ports 309~312, the voltage at the imaging device 110 may be undesirably reduced due to power losses in the cable. To prevent this voltage loss, the remote sensed voltage is provided as analog feedback to the power supply 307 circuits to adjust the output voltage to compensate for the loss.

Connection to the memory 303 is made through interface 321, and memory 303 may be used to momentarily hold data from the transducer prior to sending over an interconnect 322 that may comprise a PCIe bus. This memory 303 acts as an elastic buffer to compensate for any difference in data rate or timing of the transducer interface data from the interconnect 315 and the interconnect 322. The use of an elastic buffer also allows for different bit widths between the transducer interface bus of the interconnect 315 and the interconnect 322. In this example, the transducer interface bus has 24 streams whereas the PCIe interface had 16 lanes.

Data are provided to and from the controller 120 by interconnect 322, which connects the DTI 206 to the controller 120 through the connector 308. Because of the comparatively large data rate requirements to exchange data between the controller 120 and the imaging device 110, interconnect 322 is also a comparatively high data rate interconnect (e.g., a PCIe or similar comparatively high data rate interconnect). In accordance with a representative embodiment, upon selection of the desired imaging device 110 by the user through the computer system 115, an identification signal is sent from the imaging device 110 over the $I^2C$ bus 314 to the computer system 115. Upon receipt of this identification signal from the imaging device 110, the controller 120 sends control and data signals through the interconnect 322 to activate the needed switches of the switching circuit 301 as determined in the controller 302 to engage the selected one of the plurality of transducer ports 309~312. Once the switches are engaged, imaging is initiated and data are transferred between the imaging device 110 and the controller 120 via the DTI 206 of the US imaging system. Interconnect 322 is selected to be compatible with the selected transmission platform of the DTI 206. For example, in view of the comparatively high demands of bandwidth for reception of digital echo output data from the imaging device 110, the interconnect 322 is illustratively a PCIe or similar comparatively high data rate interconnect. Similarly, in order to transmit control and data signals from the controller 120 to the imaging device 110 via the controller 302, the interconnect 322 is illustratively a PCIe or similar comparatively high data rate interconnect. Moreover, interconnect 322 provides a plurality of data streams originating through the selected one of the plurality of transducer ports 309~312 to enable data transmission/reception at combined data rate greater than approximately 20 Gbps as contemplated by the present teachings. Again, by way of illustration, when implemented according to the PCIe protocol, interconnect 322 may have as many as 16 lanes to provide the plurality of data streams at the needed data transmission rates to carry out the desired imaging by the US imaging system 100.

The representative embodiments to this point have been described using switching circuit 301 to effect the proper connections between the controller 120 of the US imaging system 100 to the imaging device 110 using a selected one of the plurality of transducer ports 309~312 at a time. It is noted that this is merely illustrative, and the present teachings contemplate use of a multiplexer 330 in the controller 302 in lieu of interconnect 315 alone, a plurality of interconnects 315, 326, 327 and 328 provide digital echo data streams from respective ones of transducer ports 309, 310, 311 and 312. In this embodiment, each of the interconnects 315, 326, 327 and 328 is connected to a respective one of the plurality of transducer ports 309, 310, 311 and 312. Interconnects 326, 327 and 328 are substantially identical to interconnect 315, and as such are selected to enable data transmission/reception at data rate greater than approximately 20 Gbps as contemplated by the present teachings. Again, by way of illustration, when implemented in accordance with this embodiment, interconnects 326, 327 and 328 may have as many as 32 lanes to provide the plurality of data streams at the needed data transmission rates to carry out the desired imaging by the US imaging system 100.

In the illustrative embodiment, the multiplexer 330 is adapted to select data streams from the currently selected one of the plurality of transducer port 309~312 that is engaged at a particular time. During operation, each data stream from the transducer ports 309, 310, 311 and 312 is received by a respective receiver 329 of the controller 302. The multiplexer 330 is then adapted to select one of the interconnects 315, 326, 327 or 328 to receive the data streams corresponding to the selected one of the plurality of transducer port 309~312. These output echo data are then transmitted from the multiplexer as output echo data 331 from the DTI 206 to the controller 120 of the US imaging system 100. Output echo data 331 is temporarily stored in memory 303 until interconnect 322 is available to send to controller 120.

Figure 4A:
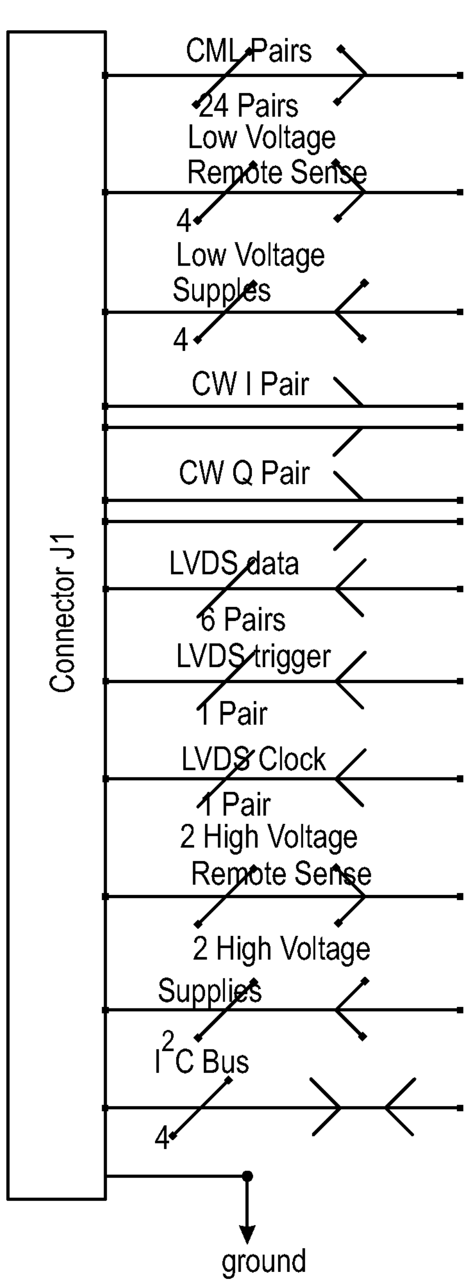
FIG. 4A is a simplified schematic block diagram of one of the plurality of transducer ports of the DTI according to a representative embodiment.

FIG. 4A is a simplified schematic block diagram of one of the plurality of transducer ports 309~312 of the DTI 206 according to a representative embodiment. Various aspects and details of the transducer port 309 are common to those described in connection with the US imaging system 100, imaging interface 111 and DTI 206 described above. These common aspects and details may not be repeated to avoid obscuring the presently described representative embodiments.

Notably, the identified transducer port 309 (also denoted J1) is adapted to receive control signals and data from the controller 302, and to transmit echo output data from the imaging device 110 to the controller 302. Transducer ports 310, 311 and 312 designated as J2, J3 and J4, respectively are, as noted above, substantially identical to transducer port 309. As noted above, transducer port 309 is selected to transmit all data from the imaging device 110 via interconnect 315, and all control signals and data from the controller 302 to the imaging device via interconnect 316. The transducer port 309 is selected based on the communications protocol (e.g., PCIe) selected for the transfer of data between the imaging device 110, the DTI 206 and the controller 120 of the imaging system 100. The transducer port 309 illustratively comprises 24 high speed serial data pairs using current mode logic (CML) to transmit digital data from the transducers of the imaging device 110 to the DTI 206 and the controller 120 of the imaging system 100.

The transducer port 309 also comprises connections for voltage power supplies provide power to the transducers of the imaging device. These power supplies provide illustrative voltages of 0.9V, 1.8V, 2.5V and 3.3V for various functions within the imaging device 110. As noted above, since the current draw on the various power supplies can be comparatively high voltage loss within the transducer cable assembly can result. As such, the transducer port 309 port comprises remote sense connections to sense the voltage at the imaging device. As noted above, the controller 302 is adapted to increase the power output from the power supply 307 via the connectors of the transducer port 309 to the imaging device 110 to compensate for the cable voltage loss.

The transducer port 309 also comprises CW Doppler baseband in-phase (I) and quadrature (Q) analog output connections from the imaging device 110.

The transducer port 309 also comprises a low-voltage differential signaling (LVDS) clock, trigger and programming data connections used to configure the transducers of the imaging device 110. High voltage power connections typically set to +/−35V along with associated remote sense connections are also provided each connector.

Finally, the transducer port 309 comprises a connection to an $I^2C$ bus, which provides imaging device identification and temperature monitoring. As described more fully below, the identification of the imaging device 110 selected by the user enables the configuration of the switches of the switching circuit 301 for use in accordance with the present teachings.

FIGS. 4B-4I are simplified schematic block diagrams of switches 402-409 of the switching circuit 301 of the DTI 206 according to a representative embodiment. Various aspects and details of the switches are common to those described in connection with the US imaging system 100, imaging interface 111 and DTI 206 described above. These common aspects and details may not be repeated to avoid obscuring the presently described representative embodiments.

Switches 402-409, switch signals from the system into/out of the selected transducer connector using the "select" control signal 313 provided by the controller 302. For ease of description, the switches 402-409 are configured to engage transducer port 309 (J1) as the selected active one of the plurality of transducer ports 309~312. As noted above, and described more fully below, upon the identification by the controller 120 of the particular transducer port selected, the switches 402-409 are configured to connect the various components of the DTI 206 to the selected one of the plurality of transducer ports 309~312 for operation of the imaging device 110 through the selected one of the plurality of transducer ports 309~312. As will be readily appreciated from a review of FIGS. 4A-4I, the switches 402-409 are adapted to connect to transducer ports 310 (J2), 311 (J3) and 312 (J4) based on the selected imaging device 110 being used in the imaging system 100.

Figure 4B:
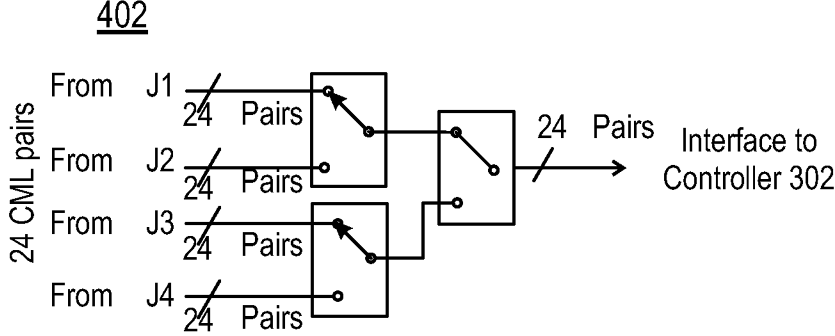
FIGS. 4B-4I are simplified schematic block diagrams of switches of a switching circuit of the DTI according to a representative embodiment.

FIG. 4B is a simplified block diagram of switch 402 that switches 24 current mode logic (CML) data pairs from the selected transducer port 309 (J1) to the interconnect 315 to the controller 302. Switch 402 comprises a plurality of switches as shown, which are compatible with the selected communication protocol of the DTI 206. Just by way of illustration, commercially available PCI gen. 3.0 compatible solid-state switches are used to switch the CML differential pairs.

Figure 4C:
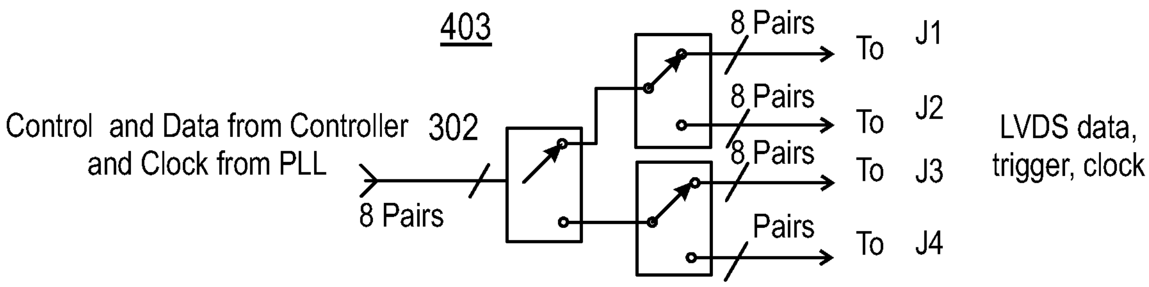

FIG. 4C is a simplified block diagram of a switch 403 adapted to switch eight (8) LVDS pairs from the controller 302 to the selected transducer port 309 (J1) corresponding to the clock signal 317, and control commands and data from interconnect 316. Again, and just by way of illustration, the switches of switch 403 comprise commercially available PCI gen. 3.0 compatible solid-state switches to switch the LVDS differential signals.

Figure 4D:
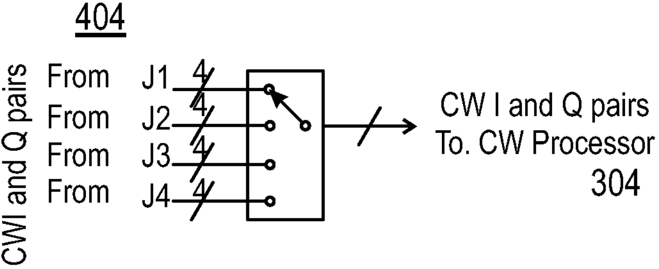

FIG. 4D is a simplified block diagram of switch 404 that comprises analog multiplexer integrated circuits to map the baseband CW signals from the selected transducer port 309 (J1) to the CW processor 304 described above.

Figure 4E:
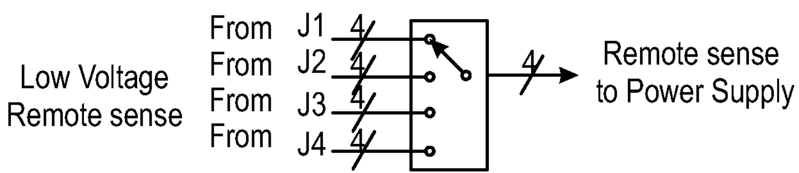

FIG. 4E is a simplified block diagram of switch 405 comprising an analog multiplexer IC to provide remote sense signals 319 that provide feedback to the power supply 307 to adjust the output voltage(s) due to IR losses along the length of the cable connection from the selected transducer port 309 to the imaging device 110.

Figure 4F:
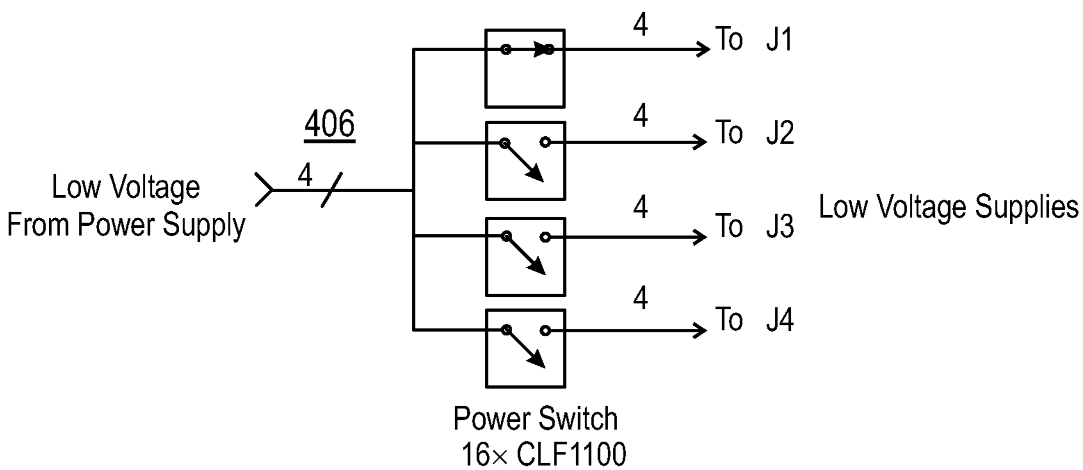

FIG. 4F is a simplified block diagram of switch 406 comprising solid state power switches to power the selected transducer port 309 with voltages (illustratively 4) from the power supply 307.

Figure 4G:
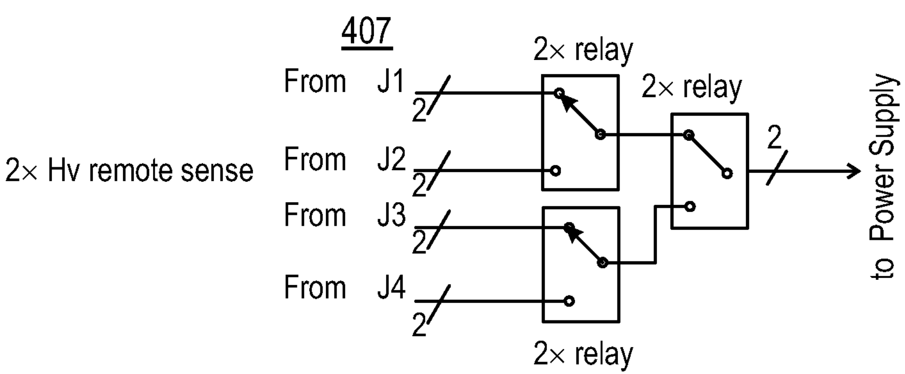

FIG. 4G is a simplified block diagram of switch 407 comprising relays to provide remote sense signals 319 for the high voltages of the power supply 307. Again, based on the measured values of the remote sense signals, the power supply 307 is adapted to adjust the output voltage provided to transducer head of the imaging device to ensure proper operation. Notably, relays are used in view of the comparatively high voltages and currents provided from the power supply 307.

Figure 4H:
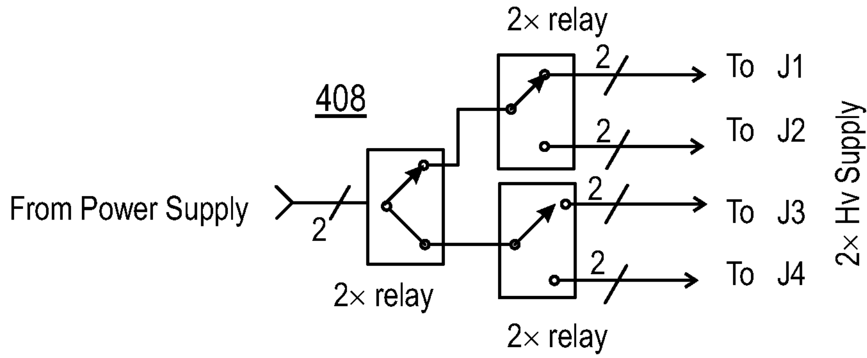

FIG. 4H is a simplified block diagram of switch 408 comprising relays to provide positive and negative high voltages from the power supply 307 to the selected transducer port 309. Relays are used in view of the comparatively high voltages and currents provided from the power supply 307.

Figure 4I:
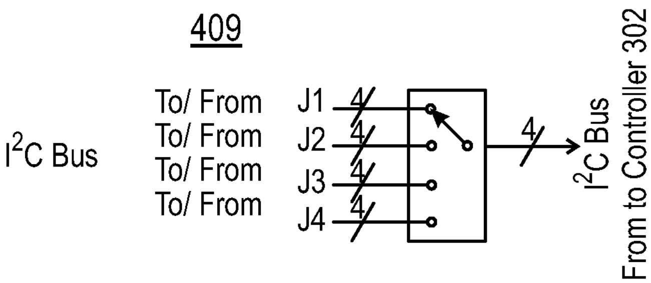

FIG. 4I is a simplified block diagram of switch 409 comprising an analog multiplexer integrated circuit to map the $I^2C$ bus from the selected transducer port to the $I^2C$ bus 314 of FIG. 3.

Figure 5:
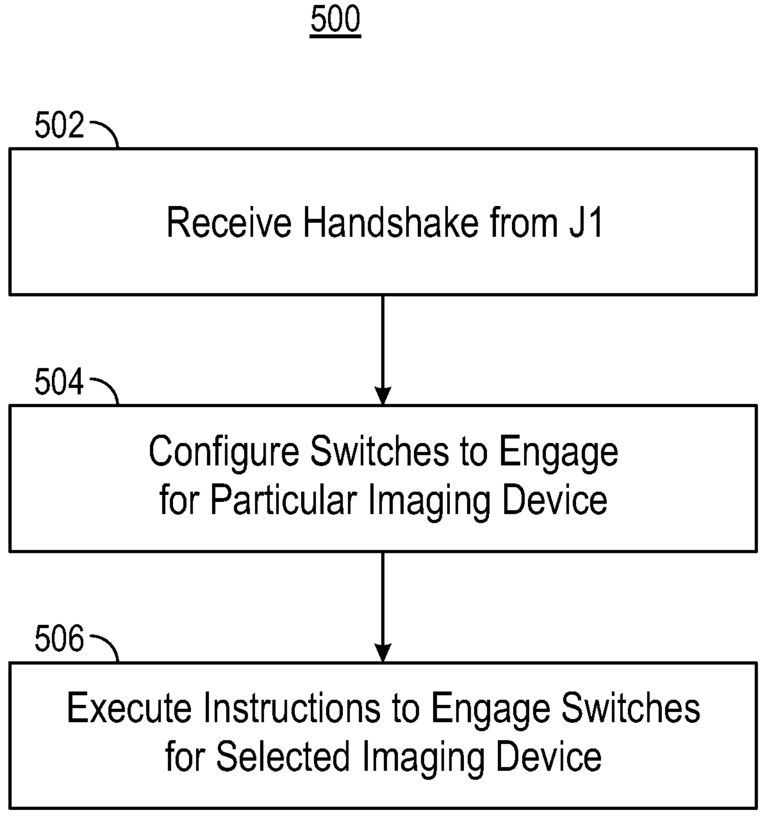
FIG. 5 is a flow-chart of a method of initiating and operating an US imaging device in accordance with a representative embodiment.

FIG. 5 is a flow-chart of a method 500 of initiating and operating an US imaging device in accordance with a representative embodiment. Various aspects and details of the method are common to those described in connection with the US imaging system 100, and is implemented using the various components of the US imaging system 100 described above. These common aspects and details may not be repeated to avoid obscuring the presently described representative embodiments.

At 502, the method 500 begins with reception of a so-called "handshake" from the selected imaging device 110 and the controller 120. Notably, upon connection to the selected one of the plurality of transducer ports 309~312, the imaging device 110 transmits identification data to the controller 120 via the communication path described above in connections with FIGS. 2-3.

At 504, the method continues with the configuration of the switches described in connection with FIGS. 4B-4I. The configuration of the switches at 504 comprises the selection of switches that need to be engaged to provide the connection to the selected one of the plurality of transducer ports 309~312 is determined by the controller 302. In accordance with a representative embodiment, instructions (code) stored in memory 303 are executed by the controller to determine the necessary connections of the various switches to establish the requisite electrical connections between the imaging device 110 and the computer system 115 of the US imaging system 100.

At 506, the method continues with the execution to engage the switches determined in 504. The controller 302 transmits commands to the switching circuit to engage the determined switches described in connection with FIGS. 4B-4I required to provide the connection to the selected one of the plurality of transducer ports 309~312. In accordance with a representative embodiment, instructions (code) stored in memory 303 are executed by the controller to effect the necessary connections of the various switches to establish the requisite electrical connections between the imaging device 110 and the computer system 115 of the US imaging system 100.

As will be appreciated by one of ordinary skill in the art having the benefit of the present disclosure, devices, systems and methods of the present teachings provide the transmission of echo image data from an ultrasound device. For example, compared to known methods and systems, various aspects of a protocol including the beginning, duration and termination of a step in the protocol can be facilitated during the generation of the protocol, or during implementation of the protocol, or both. Moreover, errors that can result from human interaction with an imaging system can be reduced thereby reducing the need to repeat procedures, and reducing the time required to complete an imaging procedure. Notably, these benefits are illustrative, and other advancements in the field of medical imaging will become apparent to one of ordinary skill in the art having the benefit of the present disclosure.

Although methods, systems and components for making comparatively high data rate connections to ultrasound imaging devices have been described with reference to several exemplary embodiments, it is understood that the words that have been used are words of description and illustration, rather than words of limitation. Changes may be made within the purview of the appended claims, as presently stated and as amended, without departing from the scope and spirit of the protocol implementation of the present teachings. The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure.

Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An ultrasound imaging system, comprising:

an ultrasound imaging device comprising a transducer; and a digital transducer interface (DTI) comprising: a plurality of transducer ports each comprising a plurality of digital data streams adapted to receive and transmit digital echo output data from the ultrasound imaging device, the transducer ports being adapted to connect to the ultrasound imaging device; a switching circuit connected to each of the plurality of transducer ports; and a controller adapted to control switches of the switching circuit to transmit digital input data to and the digital echo output data from one of the plurality of transducer ports at a time.

2. The ultrasound imaging system of claim 1, further comprising a memory that stores instructions, which when executed by the controller causes the controller to control the switches of the switching circuit to transmit the digital input data to and the digital echo output data from the one of the plurality of transducer ports at a time.

3. The ultrasound imaging system of claim 1, wherein connections between the DTI and the ultrasound imaging device comprise a connector adapted to transfer data at a combined data rate of at least 20 Gbps for the plurality of digital data streams.

4. The ultrasound imaging system of claim 3, wherein the connector comprises a peripheral component interconnect express (PCIE) connector.

5. The ultrasound imaging system of claim 1, wherein the controller comprises a field programmable gate array (FPGA).

6. The ultrasound imaging system of claim 5, wherein the switching circuit comprises a multiplexer circuit disposed in the FPGA.

7. The ultrasound imaging system of claim 1, wherein the DTI further comprises an analog processor adapted to receive continuous wave (CW) data from the switching circuit.

8. The ultrasound imaging system of claim 1, further comprising:

a power supply configured to provide voltage to the switching circuit and thereby to the one of the plurality of transducer ports; and a remote sense signal path from the one of the plurality of transducer ports to the power supply and configured to provide a measured voltage level at the transducer to the power supply, wherein the power supply is configured to adjust the provided voltage based on the measured voltage level.

9. A digital transducer interface (DTI) comprising:

a plurality of transducer ports each comprising a plurality of digital data streams adapted to receive and transmit digital echo output data from an ultrasound transducer, the transducer ports being adapted to connect to the ultrasound transducer; a switching circuit connected to each of the plurality of transducer ports; and a controller adapted to control switches of the switching circuit to transmit digital input data to and the digital echo output data from one of the plurality of transducer ports at a time.

10. The DTI of claim 9, further comprising a memory that stores instructions, which when executed by the controller causes the controller to control the switches of the switching circuit to transmit the digital input data to and the digital echo output data from the one of the plurality of transducer ports at a time.

11. The DTI of claim 9, wherein connections between the DTI and the ultrasound transducer comprise a connector adapted to transfer data at a combined data rate of at least 20 Gbps for the plurality of digital data streams.

12. The DTI of claim 9, wherein the controller comprises a field programmable gate array (FPGA).

13. The DTI of claim 12, wherein the switching circuit comprises a multiplexer circuit disposed in the FPGA.

14. The DTI of claim 9, further comprising an analog processor adapted to receive continuous wave (CW) data from the switching circuit.

15. The DTI of claim 9, wherein the switching circuit further comprises a single active connector and a switch adapted to connect a control signal from the controller to the single active connector.

16. The digital transducer interface (DTI) of claim 9, further comprising:

a power supply configured to provide voltage to the one of the plurality of transducer ports via the switching circuit; and a remote sense signal path from the one of the plurality of transducer ports to the power supply and configured to provide a measured voltage level at the ultrasound transducer to the power supply, wherein the power supply is configured to adjust the provided voltage based on the measured voltage level.

17. A method of initiating and operating an ultrasound imaging system having a digital transducer interface, the digital transducer interface comprising a plurality of transducer ports, the method comprising:

receiving a handshake from a selected port of the digital transducer interface;

determining switches to engage for a particular transducer; and executing instructions to engage the switches for the selected port connected to the imaging transducer.

* * * * *